(12) United States Patent
Gurumoorthy

(10) Patent No.: US 12,260,949 B2
(45) Date of Patent: Mar. 25, 2025

(54) SYSTEMS, METHODS, AND DEVICES FOR CUSTOM SLEEP AGE IMPLEMENTATION

(71) Applicant: StimScience Inc., Berkeley, CA (US)

(72) Inventor: Ram Gurumoorthy, Lafayette, CA (US)

(73) Assignee: STIMSCIENCE INC., Berkeley, CA (US)

(*) Notice: Subject to any disclaimer, the term of this patent is extended or adjusted under 35 U.S.C. 154(b) by 994 days.

(21) Appl. No.: 17/313,962

(22) Filed: May 6, 2021

(65) Prior Publication Data

US 2022/0059210 A1     Feb. 24, 2022

Related U.S. Application Data

(63) Continuation-in-part of application No. 17/000,220, filed on Aug. 21, 2020, now Pat. No. 11,938,275.

(51) Int. Cl.
*G16H 50/30*     (2018.01)
*A61B 5/00*     (2006.01)
(Continued)

(52) U.S. Cl.
CPC ............. *G16H 20/40* (2018.01); *G16H 50/30* (2018.01); *G16H 50/50* (2018.01); *A61B 5/4806* (2013.01); *A61M 21/02* (2013.01)

(58) Field of Classification Search
CPC . A61M 21/00–02; A61B 5/4806–4818; G16H 50/30; G16H 50/50
See application file for complete search history.

(56) References Cited

U.S. PATENT DOCUMENTS 11,938,275 B2    3/2024   Gurumoorthy
2010/0197996 A1   8/2010   Cornel
(Continued)

FOREIGN PATENT DOCUMENTS

CN      109260566     1/2019
EP       3960070       3/2022
(Continued)

OTHER PUBLICATIONS

Al Zoubi et al., "Predicting Age From Brain EEG Signalsâ€”A Machine Learning Approach," Front. Aging Neurosci., Jul. 2018, 10:184 (Year: 2018).*
(Continued)

*Primary Examiner* — Thaddeus B Cox
(74) *Attorney, Agent, or Firm* — SCHWEGMAN LUNDBERG & WOESSNER, P.A.

(57) ABSTRACT

Provided are systems, methods, and devices for implementation of custom sleep age profiles. Methods include generating at least one sleep model based, at least in part, on reference data, the at least one sleep model being configured to identify an estimated sleep age based on an input. Methods further include receiving measurement data comprising data values representing measurements of neural activity of at least one user, and generating an estimated sleep age of the at least one user based, at least in part, on the at least one sleep model and the received measurement data. Methods also include generating a plurality of stimulation parameters based, at least in part, on the estimated sleep age, the plurality of stimulation parameters being configured to modify the estimated sleep age of the at least one user.

20 Claims, 9 Drawing Sheets

(51) Int. Cl.
    *A61M 21/02*     (2006.01)
    *G16H 20/40*     (2018.01)
    *G16H 50/50*     (2018.01)

(56) References Cited

U.S. PATENT DOCUMENTS

| | | |
|---|---|---|
| 2013/0303837 A1 | 11/2013 | Berka et al. |
| 2014/0316191 A1 | 10/2014 | Zambotti et al. |
| 2016/0176409 A1 | 6/2016 | Kirsch et al. |
| 2016/0270717 A1 | 9/2016 | Luna et al. |
| 2016/0270718 A1* | 9/2016 | Heneghan ............... A61B 7/003 |
| 2017/0000970 A1 | 1/2017 | Molina et al. |
| 2019/0099009 A1 | 4/2019 | Connor |
| 2019/0126033 A1 | 5/2019 | Pradeep |
| 2019/0231256 A1 | 8/2019 | Jantunen |
| 2019/0282812 A1 | 9/2019 | Simons et al. |
| 2020/0113344 A1 | 4/2020 | Youngblood et al. |
| 2020/0234814 A1 | 7/2020 | Theory et al. |
| 2021/0315907 A1* | 10/2021 | Zasloff ................. A61K 31/575 |
| 2022/0054795 A1 | 2/2022 | Gurumoorthy |
| 2024/0165371 A1 | 5/2024 | Gurumoorthy |

FOREIGN PATENT DOCUMENTS

| | | | |
|---|---|---|---|
| JP | 2006227014 A | * | 8/2006 |
| JP | 2010099173 A | * | 5/2010 |
| JP | 2012187162 A | * | 10/2012 |
| JP | 2018517995 | | 7/2018 |
| JP | 2020129188 | | 8/2020 |
| WO | 2018115277 | | 6/2018 |
| WO | 2020085553 | | 4/2020 |
| WO | 2022236234 | | 11/2022 |

OTHER PUBLICATIONS

Sun et al., "Brain age from the electroencephalogram of sleep," Neurobiology of Aging, vol. 74, Feb. 2019, pp. 112-120 (Year: 2019).*

"International Application Serial No. PCT US2022 071989, International Search Report mailed Aug. 18, 2022", 12 pgs.

"International Application Serial No. PCT US2022 071989, Written Opinion mailed Aug. 18, 2022", 4 pgs.

"U.S. Appl. No. 17/000,220, Examiner Interview Summary mailed Oct. 3, 2022", 3 pgs.

"U.S. Appl. No. 17/000,220, Response filed Oct. 5, 2022 to Non Final Office Action mailed Jun. 15, 2022", 9 pgs.

"International Application Serial No. PCT US2022 071989, International Preliminary Report on Patentability mailed Nov. 16, 2023", 6 pgs.

U.S. Appl. No. 17/000,220, Non Final Office Action mailed Jun. 15, 2022, 14 pgs.

Zambotti et al. "Magnitude of the impact of hot flashes on sleep in peri menopausal women." Fertility and sterility vol. 102,6: 1708-15.e1.doi:10.1016/j.fertnstert.2014.08.016 (Year: 2014).

European Application Serial No. 21192253.9, Search Report mailed Jan. 31, 2022, 11 pgs.

"European Application Serial No. 22799774.9, Extended European Search Report mailed Sep. 18, 2024", 13 pgs.

Mendonca, F., "A method based on cardiopulmonary coupling analysis for sleep quality assessment with FPGA implementation", Artificial Intelligence in Medicine, vol. 112, [Online]. Retrieved from the Internet: URL : https: www.sciencedirect.com science article pii S0933365721000129 pdfft?md5= 68fc9a2f5022ed27cc3f0d7520d4a0d0andpid=1-s2.0-S0933365721000129-main.pdf, (Jan. 15, 2021), Oct. 2019.

* cited by examiner

SYSTEMS, METHODS, AND DEVICES FOR CUSTOM SLEEP AGE IMPLEMENTATION

CROSS-REFERENCE TO RELATED APPLICATIONS

This application is a continuation-in-part of U.S. patent application Ser. No. 17/000,220 filed on Aug. 21, 2020, now U.S. Pat. No. 11,938,275 granted Mar. 26, 2024, which is incorporated herein by reference in its entirety for all purposes.

TECHNICAL FIELD

The present disclosure relates to mechanisms and processes directed to measurements of brain activity and the implementation of custom sleep age profiles.

BACKGROUND

Human sleep can be measured using several aspects of the human physiology including their brain activity, their heart activity, their eye activity, temperature, movement, oxygen saturation, and the like. A human brain may include neurons which exhibit measurable electrical signals when active. Accordingly, various measuring modalities, such as electrodes, may be used to measure such electrical activity. The neural activity of neurons may include many a variety of frequency components. Accordingly, such electrical activity may be measured and represented as a power spectrum in a frequency domain. Moreover, such measurements may be obtained as a user sleeps. Similarly, other measurements may be obtained, such as heart rate activity that includes a heart rate (mean, minimum or maximum over a period, mean square over a period), as well as heart rate variability (beat-to-beat, or beat-to-beat aggregated over a window of time). However, traditional techniques for measuring such electrical activity in such contexts remain limited in their ability to utilize such measurements, and more specifically, to efficiently and effectively enable custom tailoring of a user's sleep parameters.

SUMMARY

Provided are systems, methods, and devices for the implementation of custom sleep age profiles. Methods include generating, using one or more processors, at least one sleep model based, at least in part, on reference data, the at least one sleep model being configured to identify an estimated sleep age based on an input, receiving measurement data including data values representing measurements of neural activity of at least one user, and generating, using the one or more processors, an estimated sleep age of the at least one user based, at least in part, on the at least one sleep model and the received measurement data. Methods further include generating, using the one or more processors, a plurality of stimulation parameters based, at least in part, on the estimated sleep age, the plurality of stimulation parameters being configured to modify the estimated sleep age of the at least one user. Methods for estimating sleep age may be also be implemented for monitoring, tracking, and reporting a user's sleep age without modifying the identified sleep age.

In some embodiments, the reference data is aggregated from a plurality of users. In various embodiments, the at least one sleep model includes a data structure configured to map received measurement data to one of a plurality of estimated sleep ages. According to some embodiments, the estimated sleep age is generated based on a plurality of performance metrics. In some embodiments, the plurality of performance metrics includes sleep onset latency, variability of biometrics, and relative percentages of sleep stages. In various embodiments, the modifying of the estimated sleep age includes changing a sleep age of the user to a target sleep age. According to some embodiments, the stimulation parameters include multi-modal stimulation. In some embodiments, the multi-modal stimulation includes at least some of electrical stimuli, magnetic stimuli, optical stimuli, tactile stimuli, visual stimuli, and auditory stimuli. In various embodiments, methods further include generating an estimated wake age based on a wake model.

Also disclosed herein are systems that include a communications interface configured to receive measurement data including data values representing measurements of neural activity of at least one user. The systems further include a processing device configured to generate at least one sleep model based, at least in part, on reference data, the at least one sleep model being configured to identify an estimated sleep age based on an input, generate an estimated sleep age of the at least one user based, at least in part, on the at least one sleep model and the received measurement data, and generate a plurality of stimulation parameters based, at least in part, on the estimated sleep age, the plurality of stimulation parameters being configured to modify the estimated sleep age of the at least one user. Systems also include a memory device configured to store the at least one sleep model and the plurality of stimulation parameters.

In some embodiments, the at least one sleep model includes a data structure configured to map received measurement data to one of a plurality of estimated sleep ages. In various embodiments, the estimated sleep age is generated based on a plurality of performance metrics. According to some embodiments, the modifying of the estimated sleep age includes hanging a sleep age of the user to a target sleep age. In some embodiments, the stimulation parameters include multi-anodal stimulation. In various embodiments, the processing device is further configured to generate an estimated wake age based on a wake model.

Further disclosed herein are device that include a communications interface configured to receive measurement data including data values representing measurements of neural activity of at least one user. Devices further include one or more processors configured to generate at least one sleep model based, at least in part, on reference data, the at least one sleep model being configured to identify an estimated sleep age based on an input, generate an estimated sleep age of the at least one user based, at least in part, on the at least one sleep model and the received measurement data, and generate a plurality of stimulation parameters based, at least in part, on the estimated sleep age, the plurality of stimulation parameters being configured to modify the estimated sleep age of the at least one user.

In some embodiments, the at least one sleep model includes a data structure configured to map received measurement data to one of a plurality of estimated sleep ages. In various embodiments, the estimated sleep age is generated based on a plurality of performance metrics. According to some embodiments, the modifying of the estimated sleep age includes changing a sleep age of the user to a target sleep age. In some embodiments, the stimulation parameters include multi-modal stimulation.

These and other embodiments are described further below with reference to the figures.

DETAILED DESCRIPTION OF EXAMPLE EMBODIMENTS

Reference will now be made in detail to some specific examples including the best modes contemplated by the inventors. Examples of these specific embodiments are illustrated in the accompanying drawings. While the present disclosure is described in conjunction with these specific embodiments, it will be understood that it is not intended to limit the disclosure to the described embodiments. On the contrary, it is intended to cover alternatives, modifications, and equivalents as may be included within the spirit and scope of the disclosure as defined by the appended claims. In addition, although many of the components and processes are described below in the singular for convenience, it will be appreciated by one of skill in the art that multiple components and repeated processes can also be used to practice the techniques of the present disclosure.

In the following description, numerous specific details are set forth in order to provide a thorough understanding of the present invention. Particular embodiments may be implemented without some or all of these specific details. In other instances, well known process operations have not been described in detail in order not to unnecessarily obscure the disclosure.

Figure 1:
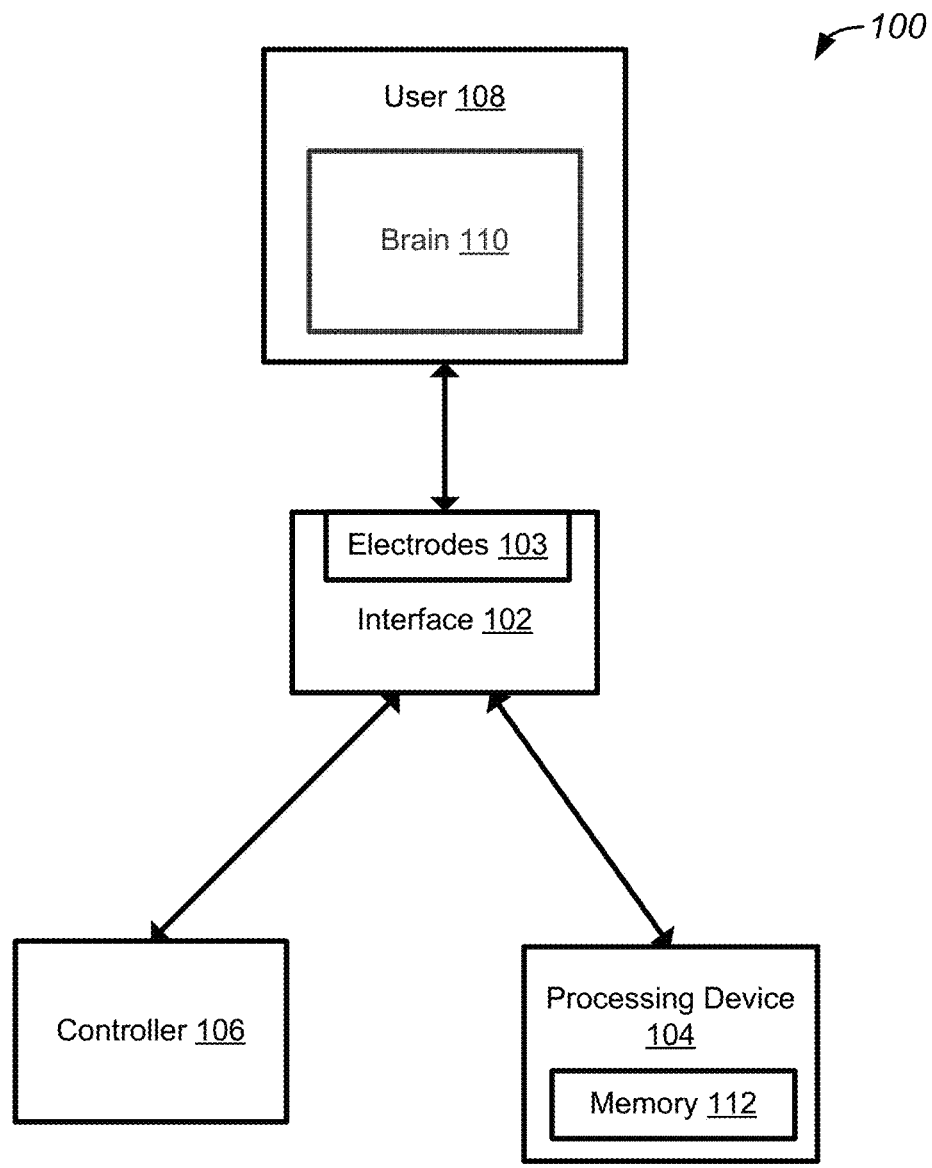
FIG. 1 illustrates an example of a system for the implementation of custom sleep parameters, configured in accordance with some embodiments.

FIG. 1 illustrates an example of a system for the implementation of custom sleep parameters, configured in accordance with some embodiments. As will be discussed in greater detail below, systems, such as system 100, may enable a user to identify target goals for their sleep profile, and subsequently have a stimulation program generated that is specifically configured to the user and the user's sleep profile, and configured to implement the identified changes to achieve the target goals for their sleep profile.

As will be discussed in greater detail below, components of system 100 may be implemented to generate custom stimulation programs to implement custom sleep targets for a user, such as user 108. As shown in FIG. 1, user 108 may be a person, and may be coupled to components of system 100. More specifically, brain 110 of user 108 may be coupled to system 100 such that system 100 is able to monitor and measure neural activity within brain 110. In some embodiments, the activity is electrical activity that is measured and recorded as electrical measurements. In this way, activity within brain 110 may be monitored during a period of sleep. As will also be discussed in greater detail below, the coupling between user 108 and system 100 may also enable stimulation of neurons within brain 110. Accordingly, system 100 may also modify neural activity of user 108.

In various embodiments, coupling between user 108 and system 100 may be implemented, at least in part, via an interface, such as interface 102. In one example, interface 102 includes a plurality of electrodes. More specifically, such electrodes may eb implemented as an electrode array. Such electrodes may be included in a scalp potential electroencephalogram (EEG) array, may be deep brain stimulation (DBS) electrodes such as electrodes used with intracranial electroencephalography, or may be an epidural grid of electrodes. In other examples, the electrodes may include optogenetics mechanisms for monitoring various neuronal processes or blood saturation. Mechanisms may be used to make various measurements and acquire measurement signals corresponding to neural activity, heart activity, temperature, body/head/eye movements. As used herein, neural activity may refer to spiking or non-spiking activity/potentiation. Moreover, heart activity may be a measure of beat rate or beat-to-beat variability. Furthermore, eye movements may include micro and macro saccades, as well as slow and rapid eye movements.

In various embodiments, such measured signals may be electrical signals derived based on neural activity that may occur in cortical tissue of a brain or may include electrical and optical signals derived from the peripheral parts of the user. Such measurements may be acquired and represented in a time domain and/or frequency domain. In this way, activity may be monitored and measured over one or more temporal windows, and such measurements may be stored and utilized by system 100. In various embodiments, such neural activity may be observed for particular regions of cortical tissue determined, at least in part, based on a configuration of interface 102. In one example, this may be determined based on a configuration and location of electrodes included in interface 102 and coupled with the brain.

According to some embodiments, one or more components of interface 102 are configured to provide stimuli to the brain coupled with interface 102. For example, one or more electrodes included in interface 102 may be configured to provide electrical stimuli to cortical tissue of the brain. As discussed above, such electrodes may be implemented utilizing one or more of various modalities which may be placed on a user's scalp, or implanted in the user's brain.

As will be discussed in greater detail below, such actuation and stimuli provided by interface 102 may be of many different modalities. For example, stimuli may be aural, visual, and/or tactile as well as being electrical and/or magnetic, or any suitable combination of these. Accordingly, interface 102 may further includes additional components, such as speakers, lights, display screens, and mechanical actuators that are configured to provide one or more of aural, visual, and/or tactile stimuli to a user. In this way, any suitable combination of different modalities may be used. For example, a combination of electrical and aural stimuli may be provided via interface 102. Further still, interface 102 may include different portions corresponding to signal acquisition and stimuli administration. For example, a first portion of interface 102 may include electrodes configured to measure neural activity, while a second portion of interface 102 includes speakers configured to generate aural stimuli. In another example, a third portion of interface 102 may include electrodes to measure ECG or heart rate, while a fourth portion may include sensors to measure oxygen saturation.

In some embodiments, interface 102 further includes one or more dedicated processors and an associated memory configured to obtain and store the measurements acquired at interface 102. In this way, such measurements may be stored and made available to other system components which may be communicatively coupled with interface 102.

System 100 further includes processing device 104 which may be configured to receive measurements made by interface 102, and may be further configured to generate sleep parameters and stimulation parameters that may be applied to user 108. As will be discussed in greater detail below, processing device 104 is configure to receive input parameters from user 108, and generate sleep parameters that identify specific changes to be made to implement the target goals specified by the user. Moreover, processing device 104 is further configured to generate stimulation parameters that are configured to identify specific sets of stimuli to be applied to implement the identified changes underlying the target goals. In various embodiments, the stimulation parameters may be included in a stimulation program which may be used to generate one or more control signals. In various embodiments, the generation of sleep parameters may include the translation of qualitative goals identified by user 108 to quantitative goals that may be mapped to specific stimulation parameters. Moreover, processing device 104 may be configured to retrieve measurement data from one or more data sources, which may be a memory device or a database system, and is further configured to retrieve measurement data obtained from the user.

As will also be discussed in greater detail below, processing device 104 is further configured to generate one or more result objects that may be included in a user interface and displayed in a display device. In various embodiments, the result objects are configured to represent a summary of the results of the application of a custom sleep program. More specifically, the result objects may be configured to represent a result or effect of the application of stimulation parameters that were generated based on identified target sleep goals. Accordingly, processing device 104 is additionally configured to generate a user interface, such as a control panel, that is configured to display an output to a user, and receive an input form the user via one or more data fields. As will be discussed in greater detail below, the user interface is configured to include various user interface elements that are configured to receive input parameters representative of target sleep goals. In some embodiments, processing device 104 includes memory device 112 which is configured to store quality assessment metrics and result objects, such as reports, generated by processing device 104.

In some embodiments, system 100 includes controller 106 which is configured to generate one or more control signals for interface 102, and is also configured to receive measurements from interface 102. Accordingly, controller 106 may be configured to implement and control the application of one or more stimulation programs and underlying stimulation parameters. In various embodiments, controller 106 is communicatively coupled with interface 102, and processing device 104. Accordingly, controller 106 is configured to received inputs from various other system components, and generate signals provided to interface 102 based, at least in part on such inputs. As will be discussed in greater detail below, such outputs may be used to provide actuations to the brain coupled with interface 102. For example, outputs generated by controller 106 may be used to stimulate the brain via one or more components of interface 102. In this way, controller 106 may provide stimuli to the brain via interface 102, may receive sleep information via other components such as processing device 104, and may generate stimuli based on such received information.

In some embodiments, controller 106 is configured to implement combined control of pharmacological and stimulation inputs. Accordingly, controller 106 may be configured to modify stimulation inputs based on an expected effect of one or more pharmacological agents that may be administered in conjunction with the stimulation. In this way, controller 106 may modify and control administration of stimuli via interface 102 based on an identified pharmacological regimen. In various embodiments, controller 106 is optionally included in system 100. For example, system 100 might not include controller 106, and such generation of control signals and receiving of measurements may be implemented by processing device 104.

Figure 2:
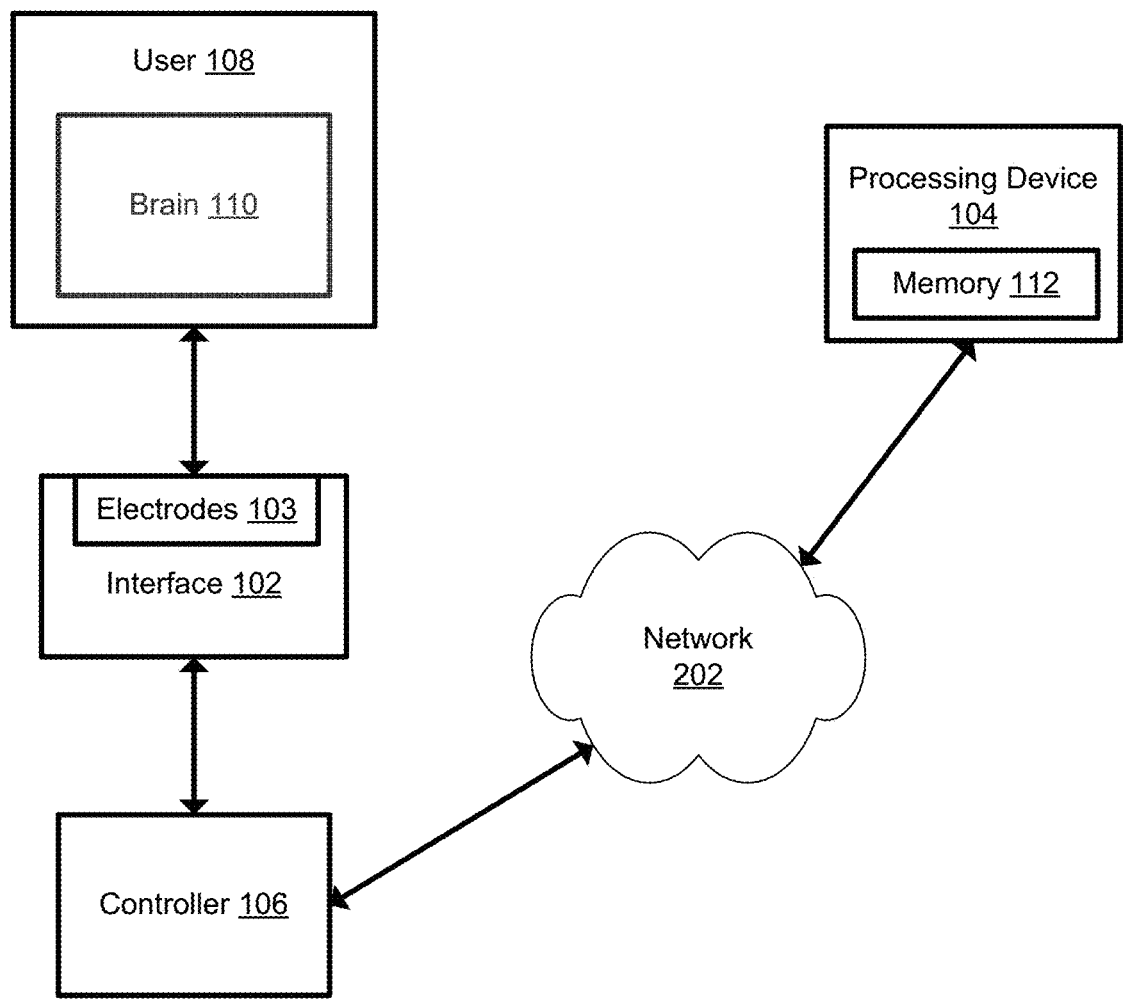
FIG. 2 illustrates another example of a system for the implementation of custom sleep parameters, configured in accordance with some embodiments.

FIG. 2 illustrates another example of a system for the implementation of custom sleep parameters, configured in accordance with some embodiments. As similarly discussed above, a user may identify target goals for their sleep profile, and subsequently have a stimulation program generated that is specifically configured to the user and the user's sleep profile. Moreover, systems, such as system 200, may include components such as interface 102, processing device 104, and controller 106, which may be coupled to a user, such as user 108.

As shown in FIG. 2, components of system 200 may be implemented in a distributed manner. For example, controller 106 may be collocated with user 108 and may be communicatively coupled to processing device 104 via a communications network, such as network 202. In this way, controller 106 may be implemented as a wireless device, such as a wearable device, at user 108, processing device 104 may be implemented remotely in a data processing system, and communications between controller 106 and processing device 104 may be handled via a network 202, which may be the internet. In this way, processing device 104 may be implemented as a personal computer or mobile device located near user 108, or processing device may be implemented as part of a distributed computing platform configured to provide sleep profile enhancement as a Software as a Service (Saas) platform.

Figure 3:
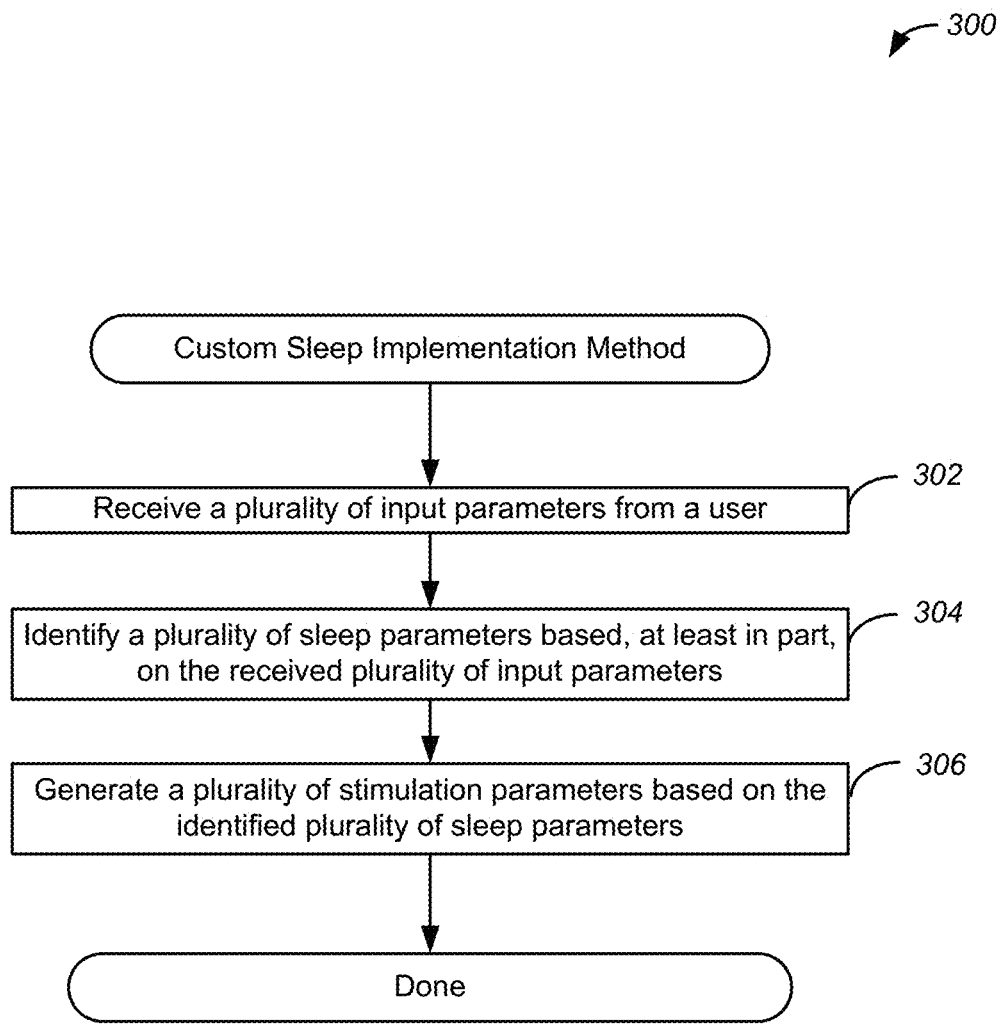
FIG. 3 illustrates an example of a flow chart of a method for the implementation of custom sleep parameters, implemented in accordance with some embodiments.

FIG. 3 illustrates an example of a flow chart of a method for the implementation of custom sleep parameters, implemented in accordance with some embodiments. As will be discussed in greater detail below, a method, such as method 300, may enable a user to identify target goals for their sleep profile, and subsequently have a stimulation program generated that is specifically configured to the user and the user's sleep profile, and configured to implement the identified changes to achieve the target goals for their sleep profile.

Accordingly, method 300 may commence with operation 302 during which a plurality of input parameters may be received from a user. In various embodiments, the input parameters are parameters that are configured to identify particular aspects of a user's sleep profile that the user intends to adjust or modify. As will be discussed in greater detail below, a user's sleep profile may characterize various aspects and signatures of the user's sleep pattern. Accordingly, the input parameters may identify various qualitative aspects of the user's sleep profile that the user intends to adjust, and further identifies the intended changes that the user would like to make.

Method 300 may proceed to operation 304 during which a plurality of sleep parameters may be identified based, at least in part, on the received plurality of input parameters. In various embodiments, the sleep parameters are configured to identify specific aspects, such as biomarkers, of the user's sleep profile that should be adjusted. Accordingly, during operation 304 specific biomarkers may be identified, as well as desired changes to such biomarkers.

Method 300 may proceed to operation 306 during which a plurality of stimulation parameters may be generated based on the identified plurality of sleep parameters. In various embodiments, the plurality of sleep parameters is configured to identify specific stimulation protocol that may be applied to implement the identified changes represented by the input parameters and the sleep parameters. Accordingly, the stimulation parameters may be used to generate control signals for the purposes of implementing the appropriate stimuli, as will be discussed in greater detail below.

Figure 4:
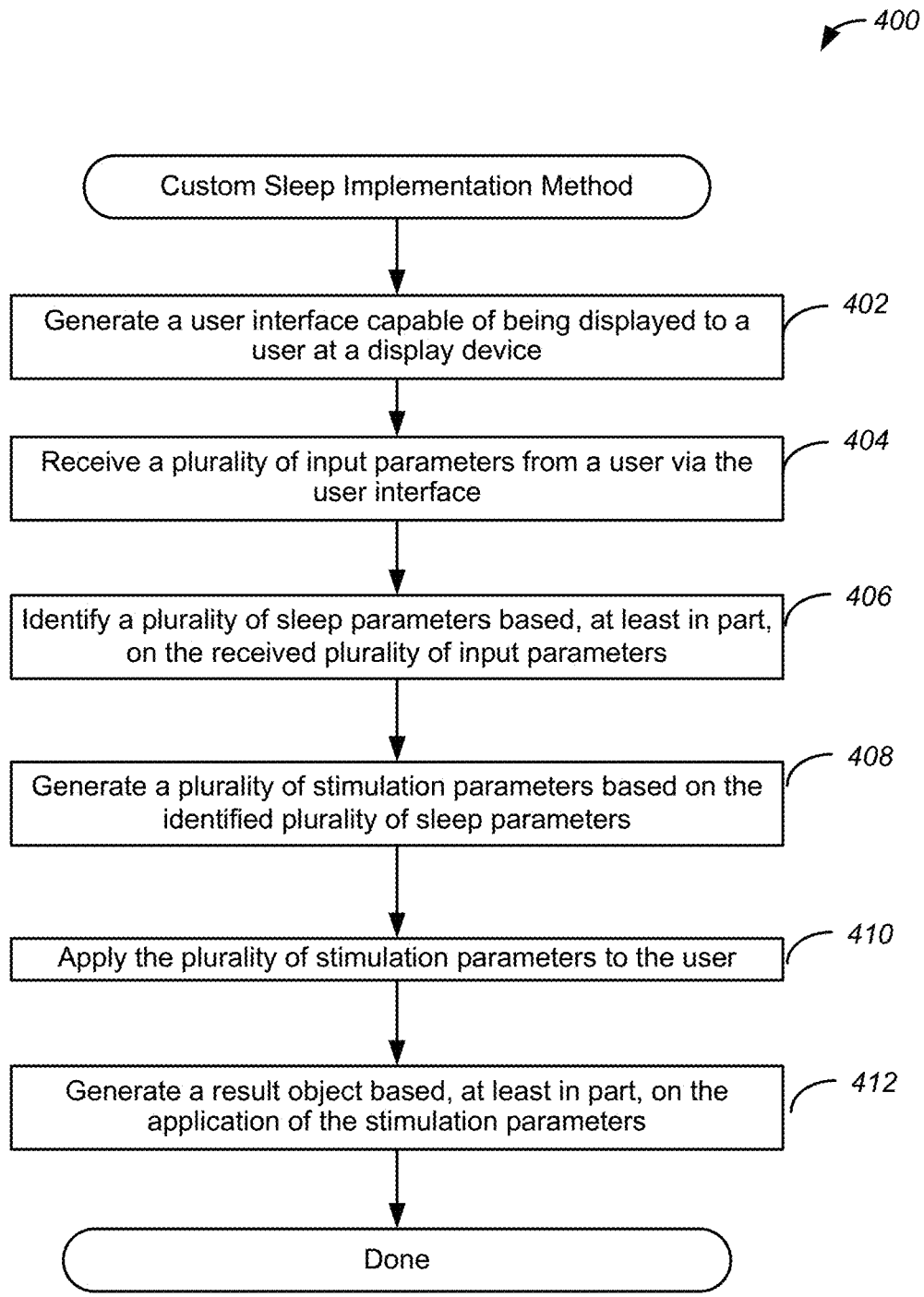
FIG. 4 illustrates another example of a flow chart of a method for the implementation of custom sleep parameters, implemented in accordance with some embodiments.

FIG. 4 illustrates another example of a flow chart of a method for the implementation of custom sleep parameters, implemented in accordance with some embodiments. As similarly discussed above a user may identify target goals for their sleep profile, and a stimulation program may be generated based on such identified target goals. As will be discussed in greater detail below, a method, such as method 400, may enable the usage of a user interface to facilitate the process, and the stimulation program may be used to provide stimulation to the user and generate a report after the application of such stimulation.

Accordingly, method 400 may commence with operation 402 during which a user interface may be generated, and the user interface may be capable of being displayed in a display device. In various embodiments, the user interface is configured to include one or more user interface elements configured to receive one or more inputs from the user. For example, the user interface may include data fields into which the user may enter text. The user interface may further include drop down menus through which the user may select one of a predetermined set of inputs. The user interface may also include sliders through which the user may select an input based on a sliding scale between two values.

In various embodiments, the user interface is configured to provide the user with a display of a plurality of aspects of the user's sleep profile that may be adjusted to implement one or more sleep goals. For example, the user interface may include a portion representing sleep latency, as well as a portion representing sleep quality. The user interface may also include portions representing more specific aspects such as sleep onset, specific sleep stage onset latency (N2 onset, N3 or deep sleep onset), total sleep duration, specific sleep stage duration, specific sleep stage duration as a % of total sleep, as well as sleep cycle durations. For example, a portion may represent a duration of a random eye movement (REM) sleep cycle. In another example, the portion may represent a duration of NREM (non REM) sleep stages. In another example, a portion could be used to specify overall sleep efficiency (total sleep time over total bed time). The user interface may also be used to specify the slow wave sleep enhancement. In this way, a particular user interface element may be generated for one or more of the above-referenced aspects of the user's sleep profile.

Moreover, each user interface element associated with each aspect of the user's sleep profile is configured to include a component configured to receive an input, such as a data field or a slider as discussed above, so that a user may provide an input that identifies a desired change to a particular aspect of the user's sleep profile. For example, a user interface component associated sleep latency may be adjusted to identify a change indicating the user wishes to decrease the time it takes the user to fall asleep. One or more changes to other parameters may also be displayed, such as a trade-off between two or more aspects of the user's sleep profile. Returning to a previous example, the user may reduce an amount of time taken to fall asleep, and this may cause an estimated reduction in the quality of the user's sleep, which may also be displayed in the user interface. In some embodiments the sleep profile parameters may be provided with a reference/baseline range which may be generated based on previous measurements for the user, or generated based on group distributions of these parameters for similar individuals, as may be determined based on biological parameters, such as age, gender, ethnicity, and health condition. The user interface may allow the user to specify their target relative to the reference/baseline ranges. For example, the user interface may be configured to present the user with sleep parameter distribution ranges based on the user's age (a sleep age profile), and let the user specify a relative sleep age of few months younger than their biological age.

Method 400 may proceed to operation 404 during which a plurality of input parameters may be received from a user. Accordingly, as discussed above, the user may provide the input parameters via the user interface, and such input parameters are configured to identify particular aspects of a user's sleep profile that the user intends to adjust or modify. Accordingly, as discussed above, the input parameters identify various qualitative aspects of the user's sleep profile that the user intends to adjust, and further identifies the intended changes that the user would like to make.

Method 400 may proceed to operation 406 during which a plurality of sleep parameters may be identified based, at least in part, on the received plurality of input parameters. As similarly discussed above, the sleep parameters are configured to identify specific aspects, such as biomarkers, of the user's sleep profile that should be adjusted. In various embodiments, biomarkers may be specific aspects of a user's sleep profile that are specific to the user's biological activity, such as a ratio of band activities, shifts in frequency spectra of activity, and a dominant resonant map of the user. Accordingly, during operation 406 specific biomarkers of the user's sleep profile may be identified, as well as desired changes to such biomarkers. Accordingly, as will be discussed in greater detail below with reference to FIG. 5, inputs provided by the user which may be represented by general descriptors may be mapped to specific biological markers and signatures of the user's sleep profile, and target changes to the biomarkers may be identified and represented in the plurality of sleep parameters.

Method 400 may proceed to operation 408 during which a plurality of stimulation parameters may be generated based on the identified plurality of sleep parameters. As similarly discussed above, the plurality of sleep parameters is configured to identify specific stimulation protocol that may be applied to implement the identified changes represented by the input parameters and the sleep parameters. Accordingly, the stimulation parameters may be used to generate control signals for the purposes of implementing the appropriate stimuli. In some embodiments, stimulation parameters may be identified based on models generated using machine learning algorithms. For example, sleep models may be developed as functional or phenomenological input-output models that can include machine learning algorithms, such as multi-variate regression, support vector machines, classifiers, deep learning neural networks, hierarchical Bayesian techniques, that are configured to learn the underlying behavior. Accordingly, previous treatment measurement data may be used to train the algorithms.

In some embodiments, the inputs to these models may include physiological measurements such as the electrical activity, heart activity, EOG, movement), self-reported measurements, and the treatment parameters, such as the stimulation modality, and the specific stimulation parameters, such as intensity and frequency. Moreover, inverse models may be generated based, at least in part, on the above models, and such inverse models may be used to predict various treatment parameters based on the desired sleep targets. These inverse models may also be customized using data specific to an individual, and from multiple treatment sessions.

Method 400 may proceed to operation 410 during which the plurality of stimulation parameters may be applied to the user. Accordingly, during a period of sleep, the stimulation parameters may be applied to the user as a sleep program configured to implement the identified changes. For example, specific stimulation frequencies (slow wave frequencies in 0.5-2 Hz, theta wave frequencies in 4-8 Hz, and alpha wave frequencies in 8-12 Hz) may affect specific changes in the user's sleep to achieve the target sleep goals. For example, if a reduced sleep latency is desired, stimulation may be applied at specific frequency band to increase the speed with which the user falls asleep. For enhancing the slow wave activity during sleep, other stimulation frequency bands can be used. Yet another frequency band stimulation can be used to improve the NREM sleep duration. In other examples, the duration of stimulation or the intensity of stimulation can impact the onset of sleep and the total sleep duration. In this way, stimulation parameters may be applied to the user while the user sleeps to implement multiple target goals for the user's sleep profile. Moreover, measurement data may also be obtained while the user sleeps. Accordingly, measurement data may be obtained to monitor the effect of the applied stimulation program.

Method 400 may proceed to operation 412 during which a result object may be generated based, at least in part, on the application of the stimulation parameters. Accordingly, the measurement data as well as previous sleep data may be retrieved and used to generate one or more result objects that represent a result of the applied stimulation. For example, if reduced sleep latency was desired, the measurement data may be used to determine how long it took the user to fall asleep. This may be compared against a similar determination made on the user's previous sleep data. The difference between the times may be represented as a result included in a result object that is capable of being displayed in the user interface. In this way, the user may be provided with a report of how effective the applied stimulation program was, and how close the user has come to the identified target goals.

Figure 5:
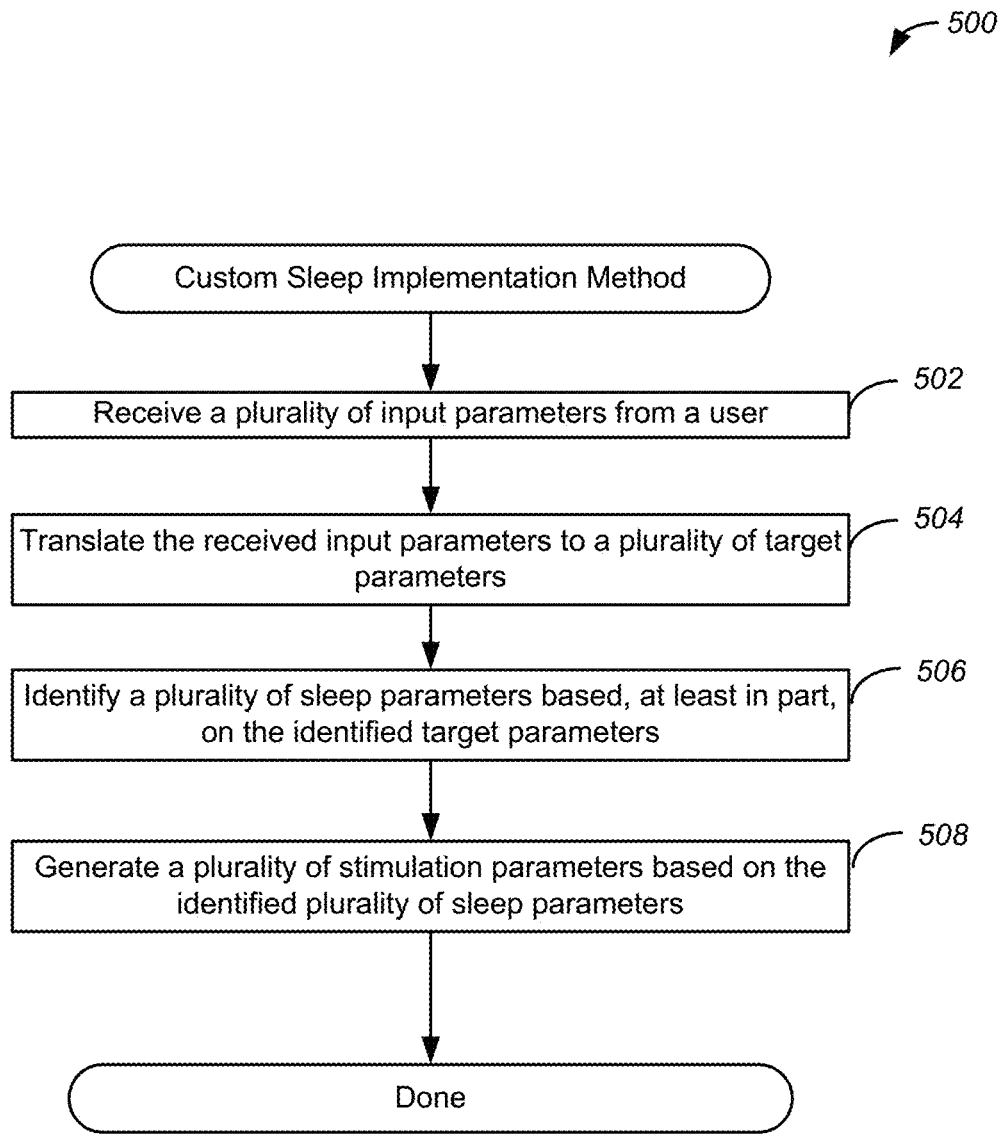
FIG. 5 illustrates an additional example of a flow chart of a method for the implementation of custom sleep parameters, implemented in accordance with some embodiments.

FIG. 5 illustrates an additional example of a flow chart of a method for the implementation of custom sleep parameters, implemented in accordance with some embodiments. As similarly discussed above a user may identify target goals for their sleep profile, and a stimulation program may be generated based on such identified target goals. As will be discussed in greater detail below, a method, such as method 500, may use one or more processing devices to translate qualitative goals to quantitative goals, and thus enhance the ease with which the user is able to identify and implement target goals for the user's sleep profile.

Accordingly, method 500 may commence with operation 502 during which a plurality of input parameters may be received from a user. As similarly discussed above, the input parameters are parameters that are configured to identify particular aspects of a user's sleep profile that the user intends to adjust or modify. Moreover, the input parameters may identify various qualitative aspects of the user's sleep profile that the user intends to adjust, and further identifies the intended changes that the user would like to make.

Method 500 may proceed to operation 504 during which the received input parameters may be translated to a plurality of target parameters. As stated above, the input parameters may be qualitative parameters that generally identify changes to be made to the user's sleep profile. During operation 504, each of the qualitative parameters may be mapped to one or more specific quantitative parameters, which may be specific biomarkers with associated stimulation parameters. In one example, a particular qualitative parameter that identifies a general target goal of reducing a sleep latency may be mapped to specific biomarkers corresponding to sleep latency. For example, the identified target parameters may include an amount of neural activity at a particular frequency band associated with a first stage of sleep. In this way, general qualitative goals may be translated or mapped to specific quantitative aspects of the user's sleep profile, and such a translation may be implemented based on a previously determined mapping stored in a storage device. In some examples, the target parameters may be specified relative to group ranges. For example, the user may specify a target sleep onset and duration corresponding to a sleep age of −2 years. In this example, the specified target parameter identifies a range that corresponds to an individual who is 2 years younger than the user's biological age, as determined based on age distributions of sleep profiles aggregated from a group of users.

Accordingly, during operation 504, the specified range may be translated to a quantitative range for the target sleep onset and duration. Moreover, such generation of a mapping and implementation of a translation may be implemented based, at least in part on the identification and usage of specific biomarkers as well as the usage of sleep models discussed above, to implement the mapping and translation. Accordingly, the sleep models discussed above may be instantiated to implement the previously described mapping and translation.

Method 500 may proceed to operation 506 during which a plurality of sleep parameters may be identified based, at least in part, on the identified target parameters. As similarly discussed above, the target parameters are configured to identify specific aspects, such as biomarkers, of the user's sleep profile that should be adjusted. Accordingly, during operation 506, specific changes to the biomarkers may be identified, and sleep parameters may be generated that identify the specified changes to the biomarkers.

Method 500 may proceed to operation 508 during which a plurality of stimulation parameters may be generated based on the identified plurality of sleep parameters. As similarly discussed above, the plurality of sleep parameters is configured to identify specific stimulation protocol that may be applied to implement the identified changes represented by the input parameters and the sleep parameters. Accordingly, the stimulation parameters may be used to generate control signals for the purposes of implementing the appropriate stimuli.

Figure 6:
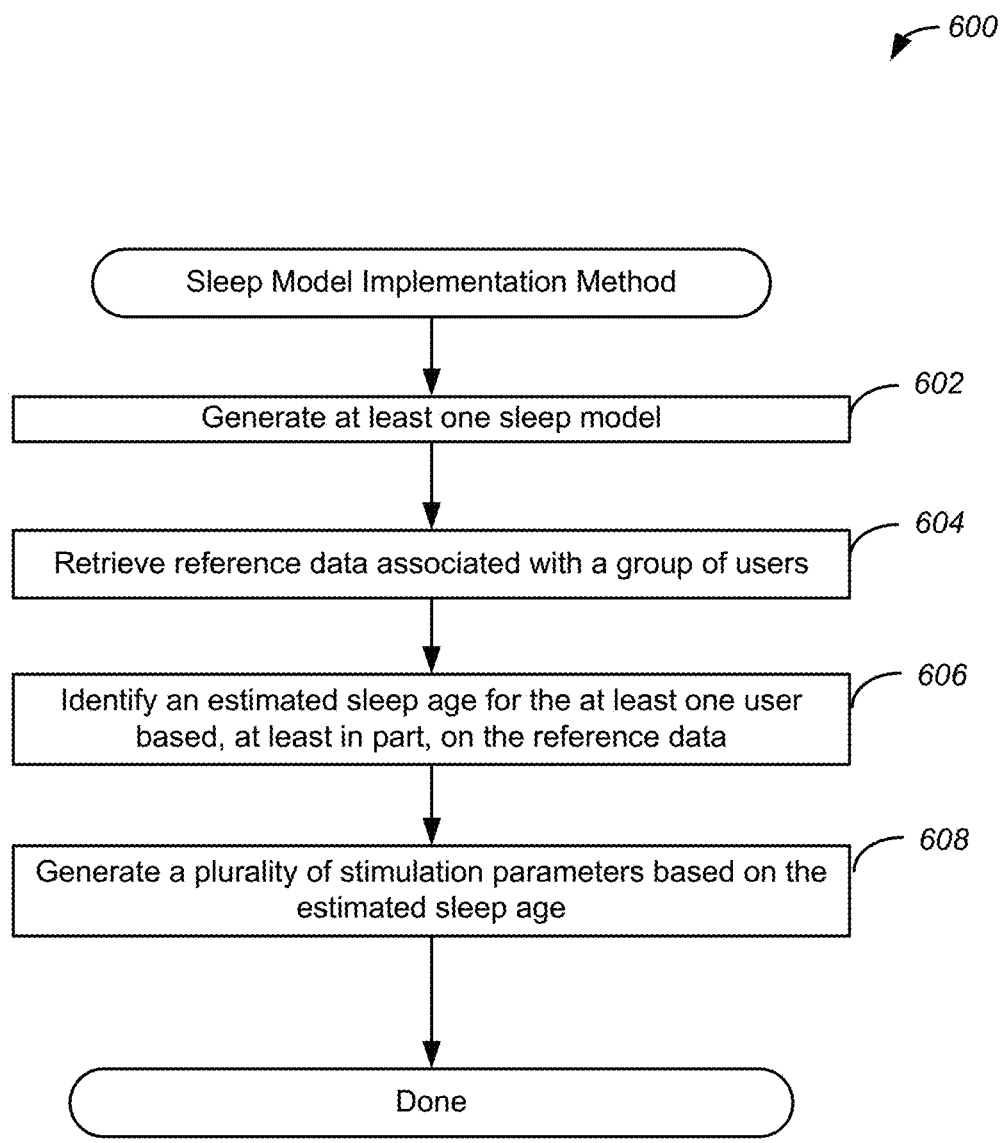
FIG. 6 illustrates an example of a flow chart of a method for the implementation of a sleep model, implemented in accordance with some embodiments.

FIG. 6 illustrates an example of a flow chart of a method for the implementation of a sleep model, implemented in accordance with some embodiments. As discussed above, sleep models may be functional or phenomenological input-output models that are configured to model a user's brain, and how various inputs, such as stimuli, may affect the user's sleep. As will be discussed in greater detail below, such sleep models may be used to estimate a user's sleep age, and further enable the generation of stimuli to modify the user's sleep age and increase the quality of the user's sleep.

Accordingly, method 600 may commence with operation 602 during which at least one sleep model may be generated. As similarly discussed above, a sleep model may be configured to include one or more models generated using machine learning algorithms. For example, sleep models may be developed as functional or phenomenological input-output models that can include machine learning algorithms, such as multi-variate regression, support vector machines, classifiers, deep learning neural networks, hierarchical Bayesian techniques that are configured to learn the underlying behavior of a user, or a group of users. Accordingly, a sleep model may be generated by training a machine learning algorithm based on a user's previous measurement data. Such previous measurement data may include measurements taken during a wake period, then during a sleep period, and then during an additional wake period. Moreover, such measurements may be made prior to, during, and after the application of various stimuli. In this way, neural activity of the user during sleep and responses of the user to stimuli may be approximated by the sleep model.

Method 600 may proceed to operation 604 during which reference data may be received. In various embodiments, the reference data may be measurement data aggregated from other users and may include measurements of neural activity of the other users during wake periods and sleep periods. Accordingly, the measurements may include various different types of measurements, as well as various metrics determined based on such measurements. Such measurements and metrics may be aggregated and averaged based on age groups of the users to generate an averaged reference profile for each age group. Additional details regarding such measurements and associated metrics are discussed in greater detail below with reference to FIG. 7. In various embodiments, the age group may be a range of years, or by individual years. It will be appreciated that any suitable measurement or unit of time may be used to define an age group.

Method 600 may proceed to operation 606 during which an estimated sleep age may be identified. Thus, during operation 606, measurement data of the user may be compared against the reference data, and an estimated sleep age may be identified based on the comparison. For example, particular aspects of the measurement data may be matched or correlated with particular aspects of the reference data, and may be mapped to an estimated sleep age. In this way, the reference data and measurement data may be used to generate an estimated sleep age. It will be appreciated that the estimate sleep age may be different than the actual biological age of the user. Additional details regarding the identification of estimated sleep ages are discussed in greater detail below with reference to FIG. 7.

Method 600 may proceed to operation 608 during which a plurality of stimulation parameters may be generated. Accordingly, during operation 608, the sleep model of the user's neural activity may be used to identify and generate particular stimulation parameters that are configured to modify and adjust the user's estimated sleep age. As will be discussed in greater detail below, in this way, the user's sleep age may be adjusted to correct the user's sleep age. For example, if the user's sleep age is identified as being older than the user's biological age, stimulation parameters may be generated to modulate particular aspects of the user's neural activity to lower the user's sleep age to match the user's biological age.

Figure 7:
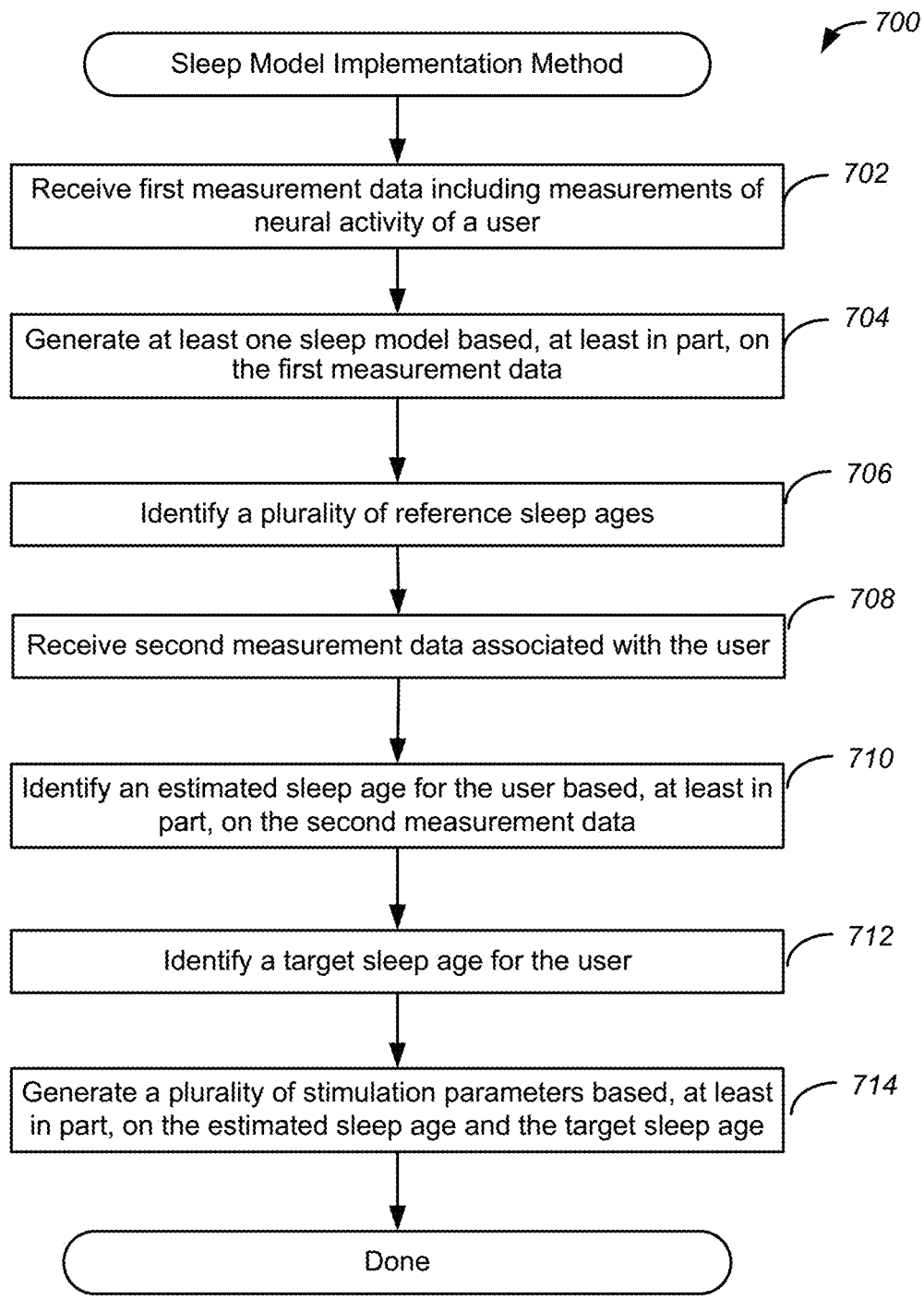
FIG. 7 illustrates an additional example of a flow chart of a method for the implementation of a sleep model, implemented in accordance with some embodiments.

FIG. 7 illustrates an additional example of a flow chart of a method for the implementation of a sleep model, implemented in accordance with some embodiments. As discussed above, sleep models may be functional or phenomenological input-output models that are configured to model a user's brain, and how various inputs, such as stimuli, may affect the user's sleep. As will be discussed in greater detail below, such sleep models may be used to estimate a user's sleep age, identify a target sleep age, and generate specific stimulation parameters that are configured to achieve the target sleep age.

Method 700 may commence with operation 702 during which first measurement data may be received. In various embodiments, the first measurement data may be previous measurement data obtained from a particular user. For example, the first measurement data may have been obtained during previous implementations of stimulation treatments, or during previous observation periods. Accordingly, historical measurement data may be stored for a particular user in a storage location, such as a database system. Moreover, such data may be stored in a user account associated with the user. In various embodiments, during operation 702, such measurement data may be retrieved.

Method 700 may proceed to operation 704 during which at least one sleep model may be generated based on the first measurement data. As discussed above, a sleep model may be configured to include one or more models generated using machine learning algorithms. More specifically, sleep models may be developed as functional or phenomenological input-output models that can include machine learning algorithms that are configured to learn the underlying behavior of a user. Accordingly, during operation 704, a sleep model may be generated by training a machine learning algorithm based on a user's retrieved first measurement data. As also discussed above, such first measurement data may include measurements taken during a wake period, then during a sleep period, and then during an additional wake period. Moreover, such first measurement data may be made prior to, during, and after the application of various stimuli. In this way, neural activity of the user during sleep and responses of the user to stimuli may be approximated by the sleep model.

Method 700 may proceed to operation 706 during which a plurality of reference sleep ages may be identified. As discussed above, reference data may be retrieved, and such reference data may be measurement data aggregated from other users. As also discussed above, such reference data may include measurements and metrics that are aggregated and averaged based on age groups of the users to generate an averaged reference profile for each age group. More specifically, the reference data may include various different measures and metrics, such as any of the biomarkers discussed above. Moreover, such measures and metrics may include other measures such as polysomnography (PSG) measurements of sleep change (for example, percent changes in time spent in particular sleep stages), an amount of slow wave activity during a particular sleep stage, an amount of high frequency activity during a particular sleep stage, as well as relative slow wave to high frequency activity ratios, and changes in such measures. Such measures may also include measurements of sleep onset latency, heart rate variability, oxygen saturation levels, as well as body movement. Moreover, the measurements may be made via one or more of multiple modalities, such as EEG or As discussed above, sleep ages may be identified based on such measurements in reference data. Accordingly, each of one or more sleep ages may be associated with a particular pattern present in the reference data. For example, a sleep age may be identified based on slow wave-high beta power spectral density relationships. In another example, a sleep age may be identified based on a sleep efficiency, as determined above. In various embodiments, sleep ages may be determined based on a combination of one or more of the previously mentioned measures. In this way, each sleep age may have a specific measurement pattern associated with it. Accordingly, during operation 706, one or more data objects may be retrieved that identify the previously discussed age groups as well as patterns of neural activity associated with each age group as determined based on the reference data.

Method 700 may proceed to operation 708 during which second measurement data may be received. Accordingly, new measurement data may be obtained from the user. As discussed above, such second measurement data may be obtained during a sleep period, and may also include portions of wake periods that are adjacent to the sleep period. For example, the second measurement data may include measured neural activity of the user during a period of time prior to the user falling asleep, during the user's sleep, and a period of time after the user wakes up. Such measurement data may be pre-processed to include various metrics and markers discussed above.

Method 700 may proceed to operation 710 during which an estimated sleep age may be identified. As similarly discussed above, during operation 710, the second measurement data of the user may be compared against the reference data and the reference sleep ages, and an estimated sleep age may be identified based on the comparison. As discussed above, particular aspects of the second measurement data may be matched or correlated with particular aspects of the reference sleep profiles, and may be mapped to a particular reference sleep age based on a correlation or match between one or more aspects of the second measurement data and the reference data. Such a determination may be made based on a statistical measure of proximity or correlation.

In some embodiments, the identification of the estimated sleep age may be implemented based on a multi-variate distribution formed based on multiple dimensions of user attributes. For or example, a multi-variate distribution may be generated based on aggregated user data from various different users. More specifically, such aggregated data may include data for each of multiple users, and the data may have multiple dimensions or attributes. As will be discussed in greater detail below, features or patterns within the distributions may be identified by aggregating or grouping users based on attributes in the user data, such as users' age. Attributes of a particular user may be compared with the multi-variate distribution, and matched to a particular value based on the comparison of attribute values. In some embodiments, one or more interpolation or extrapolation techniques may be implemented for line fitting or curve fitting. For example, raw distribution data may be fit to a mathematical function, such as a polynomial, logarithmic, or exponential curve. In some embodiments, the user multi-variate data may be matched with clusters within the underlying distribution data or interpolated data. In various embodiments, such age clusters may be determined by forming buckets within the aggregated user data, and a distance from clusters may be used to identify a user's sleep age.

In some embodiments, a parametric model may be generated based on measured input-output data, and such a parametric model may be used to match a user's data and identify a sleep age based on an output of the model. For example, the parametric model may be generated based on a family of probability distributions generated based on the measured input-output data. Such probability distributions may be used to generate a statistical model having a finite number of parameters. In various embodiments, one or more machine learning algorithms may be implemented to generate a prediction of a sleep age. For example, a neural network or deep learning network may be used to form a model that receives user measurements as an input and provides an estimated sleep age as an output. It will be appreciated that any suitable set of machine learning algorithms may be used to model and implement input-output relationships for a user.

In some embodiments, data underlying these models may include raw and/or processed data that may be measured and/or aggregated. For example, raw data may include a user's EEG measurement data, and pre-processed data may include power spectrum determined based on bands of frequency ranges. In some embodiments, a single variate technique may be implemented. For example, a biological age-based distribution of sleep efficiency may be generated and used as a model for estimating a sleep age. Accordingly, a single variate model may be used to estimate a user's sleep age based on the user's sleep measurements and efficiency.

Method 700 may proceed to operation 712 during which a target sleep age may be identified. In various embodiments, the target sleep age may be determined based, at least in part, on the user's biological age, which may be identified based on available data associated with the user, such as biological data stored in the user's account. Accordingly, the target sleep age may be the user's biological age. In some embodiments, the target sleep age may be determined based on an offset applied to the user's biological age. For example, the target sleep age may be the user's biological age minus five years. Such a determination of the target sleep age may be implemented based on one or more previously designated configuration parameters which may have been determined by an entity, such as the user or an administrator.

Method 700 may proceed to operation 714 during which a plurality of stimulation parameters may be generated. Accordingly, as similarly discussed above, during operation 714, the sleep model of the user's neural activity may be used to identify and generate particular stimulation parameters that are configured to modify and adjust the user's estimated sleep age. As will be discussed in greater detail below, in this way, the user's sleep age may be adjusted to correct the user's sleep age. For example, if the user's sleep age is identified as being older than the user's biological age, stimulation parameters may be generated to modulate particular aspects of the user's neural activity to lower the user's sleep age to match the user's biological age. Moreover, the implementation of the stimulation and the configuration of the stimulation parameters may be implemented in a closed-loop manner. As discussed above, the stimulation parameters may be configured to implement multi-modal stimulation. For example, the stimuli may be applied via tES, tMS, auditory, tactile, and/or visual stimulation, and may be applied before sleep, during sleep, and/or just after sleep.

In some embodiments, the generation of stimulation parameters may be generated based on one or modifications made to characteristic neural activity associated with particular sleep ages. For example, inversion of particular stimulation parameters may be used to generate stimulation parameters. More specifically, particular neural characteristics associated with users of a particular sleep age may be inverted to shift or modulate the user's sleep age. More specifically, a duration of specific frequencies of stimulation may be changed based on a target sleep age. For example, if a user has a biological age of 50 years and is determined to have a sleep age of 52 years, a duration of the low frequency stimulation may be increased to improve a band ratio metric, which may be a factor of sleep quality and sleep age estimation. In this example, the increased low frequency activity may be associated with younger sleep ages, and may be used as the basis of formulation of sleep parameters. Accordingly, parameters of neural activity used to define sleep ages may be used to determine which parameters should be inverted for the purposes of stimulation. In some embodiments, the amount of low frequency stimulation may be determined based on a designated amount. For example, an entity, such as an administrator, may configure the amount to initially be for half of a sleep period, and additional increments may be made in subsequent sessions if appropriate.

Figure 8:
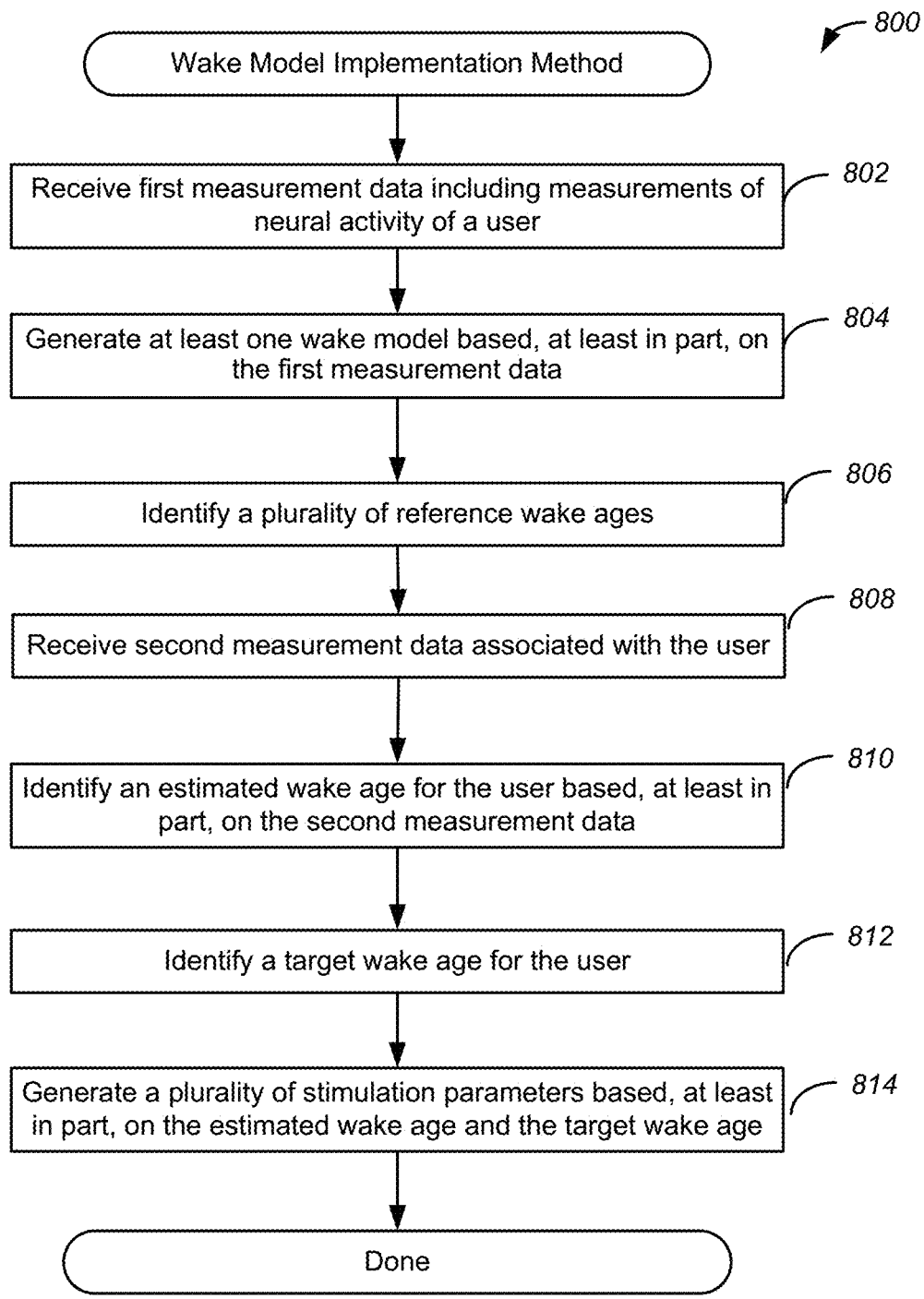
FIG. 8 illustrates an example of a flow chart of a method for the implementation of a wake model, implemented in accordance with some embodiments.

FIG. 8 illustrates an example of a flow chart of a method for the implementation of a wake model, implemented in accordance with some embodiments. As discussed above, sleep models may be functional or phenomenological models that are configured to model a user's brain. According to various embodiments disclosed herein, wake models may also be generated that model the user's neural activity and behavior when awake, and not asleep. Accordingly, as will be discussed in greater detail below, such wake models may be used to estimate a user's wake age, identify a target wake age, and generate specific stimulation parameters that are configured to achieve the target wake age.

Method 800 may commence with operation 802 during first measurement data may be received. In various embodiments, the first measurement data may be previous measurement data obtained from a particular user, and the first measurement data may have been obtained during previous implementations of stimulation treatments, or during previous observation periods. Accordingly, as discussed above, historical measurement data may be stored for a particular user in a storage location, such as a database system. In various embodiments, the first measurement data may include measurements obtained while the user is waking, while the user is going to sleep, and also while the user is performing various activities while awake. If will be appreciated that the first measurement data may include other types of measurement as well, such as user responses to surveys. In various embodiments, such data may be stored in a user account associated with the user, and during operation 802, such measurement data may be retrieved.

Method 800 may proceed to operation 804 during which at least one wake model may be generated based on the first measurement data. As similarly discussed above, a wake model may be configured to include one or more models generated using machine learning algorithms. More specifically, wake models may be developed as functional or phenomenological input-output models that can include machine learning algorithms that are configured to learn the underlying behavior of a user. Accordingly, during operation 804, a wake model may be generated by training a machine learning algorithm based on a user's retrieved first measurement data. In various embodiments, such first measurement data may include measurements taken during a sleep period, then during a wake period, and then during subsequent sleep period. Moreover, such first measurement data may be made prior to, during, and after the application of various stimuli. In this way, neural activity of the user while awake, and responses of the user to stimuli may be approximated by the wake model.

Method 800 may proceed to operation 806 during which a plurality of reference wake ages may be identified. As discussed above, reference data may be retrieved, and such reference data may be measurement data aggregated from other users. As also discussed above, such reference data may include measurements and metrics that are aggregated and averaged based on age groups of the users to generate an averaged reference profile for each age group. Accordingly, during operation 806, one or more data objects may be retrieved that identifies the previously discussed age groups as well as patterns of neural activity associated with each age group as determined based on the reference data.

In various embodiments, the reference data may identify wake ages based on measures and metrics including any of the biomarkers discussed above. Moreover, the wake ages may be determined based on waking performance assessment measures as well. Accordingly, the reference data may include measurement data of such performance assessments. For example, such measurements may include measures of users' level of alertness, refreshedness, memory consolidation, relaxedness, cognitive capacity, memory improvement, motor performance, and/or mood. These may be measured by questionnaires or behavioral tasks such as psychomotor vigilance tasks (PVT), emotion bias tasks (EBT), reaction time tasks, attention network tasks (ANT), memory recall task, and/or short-term memory tasks. Measurements may also include EEG measurements such as spectral measures of alertness, high frequency spectrum, slow wave-high beta ratio, delta-beta ratio, emotion assessment, memory and attention assessment, as well as other magnetoencephalography (MEG) measurements.

Method 800 may proceed to operation 808 during which during which second measurement data may be received. Accordingly, as similarly discussed above, new measurement data may be obtained from the user. More specifically, second measurement data may be obtained during a wake period, and may also include portions of sleep periods that are adjacent to the wake period. For example, the second measurement data may include measured neural activity of the user during a period of time prior to the user waking, while the user is awake, and a period of time after the user falls asleep. Such measurement data may be pre-processed to include various metrics and markers discussed above.

Method 800 may proceed to operation 810 during which an estimated wake age may be identified. As similarly discussed above, during operation 810, the second measurement data of the user may be compared against the reference data and the reference wake ages, and an estimated wake age may be identified based on the comparison. As discussed above, particular aspects of the second measurement data may be matched or correlated with particular aspects of the reference wake profiles, and may be mapped to a particular reference wake age based on a correlation or match between one or more aspects of the second measurement data and the reference data. As similarly discussed above, such a determination may be made based on a statistical measure of proximity or correlation.

Method 800 may proceed to operation 812 during which a target wake age may be identified. As similarly discussed above a user's target wake age may be determined based, at least in part, on the user's biological age, which may be identified based on available data associated with the user, such as biological data stored in the user's account. Accordingly, the target wake age may be the user's biological age. Moreover, as also discussed above, the target wake age may be determined based on an offset applied to the user's biological age. For example, the target wake age may be the user's biological age minus five years.

Method 800 may proceed to operation 814 during which a plurality of stimulation parameters may be generated. Accordingly, as similarly discussed above, during operation 814, the wake model of the user's neural activity may be used to identify and generate particular stimulation parameters that are configured to modify and adjust the user's estimated wake age. Moreover, the stimulation parameters may be further configured based on aspects of the user's wake period, such as a designated period of time during the day during which the user is available, and stimulation may be applied. In this way, the user's wake age may be adjusted to correct the user's wake age. For example, if the user's wake age is identified as being older than the user's biological age, stimulation parameters may be generated to modulate particular aspects of the user's neural activity to lower the user's wake age to match the user's biological age. As discussed above, the stimulation parameters may be configured to implement multi-modal stimulation.

Figure 9:
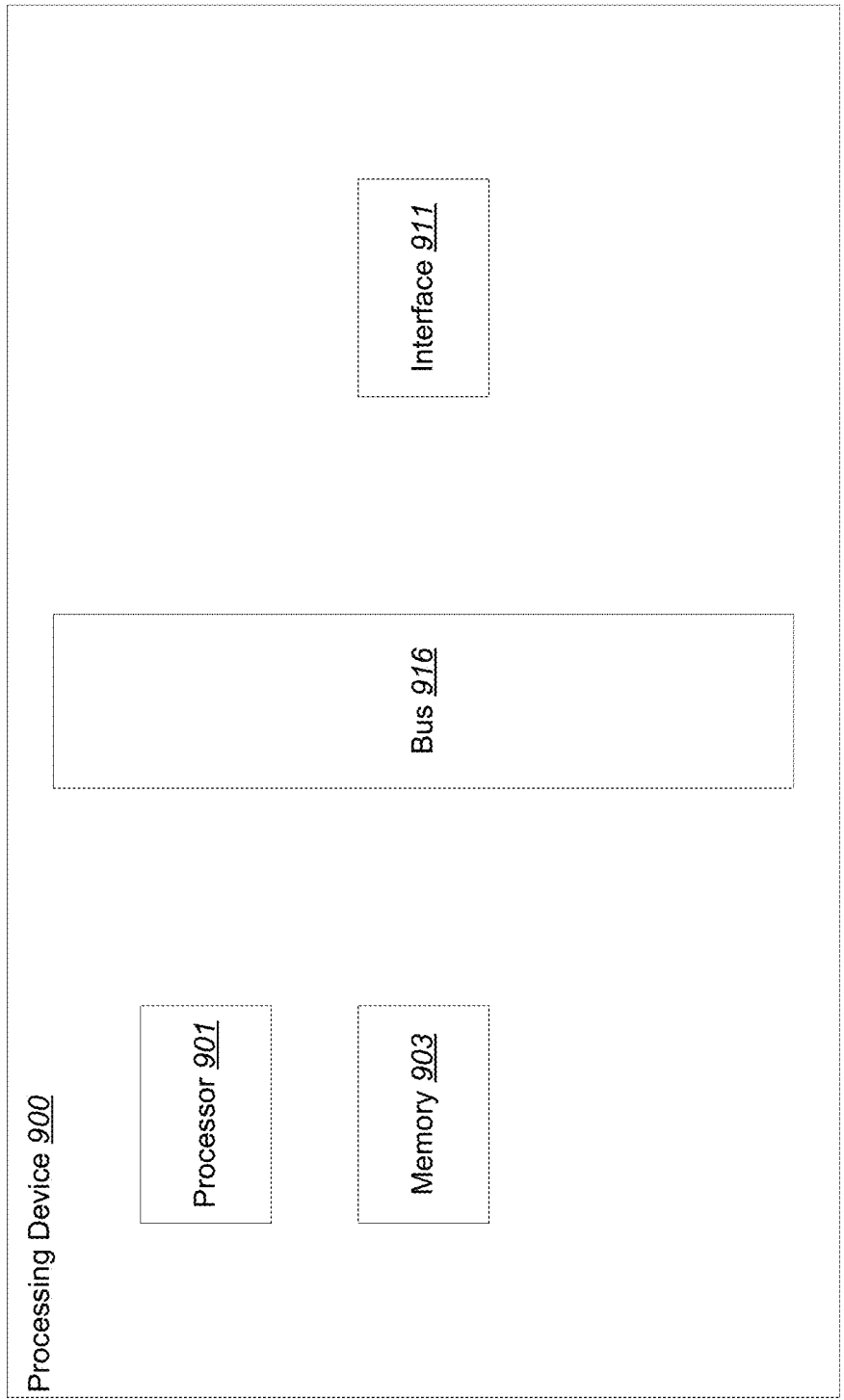
FIG. 9 illustrates an example of a processing device that can be used with various embodiments.

FIG. 9 illustrates an example of a processing device that can be used with various embodiments. For instance, the processing device 900 can be used to implement any of processing device 104 and controller 106 according to various embodiments described above. In addition, the processing device 900 shown can be implemented in conjunction with a computing system on a mobile device or on a computer or laptop, etc. According to particular example embodiments, a processing device 900 suitable for implementing particular embodiments of the present invention includes a processor 901, memory 903, an interface 911, and a bus 916 (e.g., a PCI bus). The interface 911 may include separate input and output interfaces, or may be a unified interface supporting both operations. When acting under the control of appropriate software or firmware, the processor 901 is responsible for tasks such as sleep parameter and stimulation parameter computation and generation. Various specially configured devices can also be used in place of a processor 901 or in addition to processor 901. The complete implementation can also be done in custom hardware. The interface 911 may be configured to send and receive data packets or data segments over a network. Particular examples of interfaces the device supports include Ethernet interfaces, frame relay interfaces, cable interfaces, DSL interfaces, token ring interfaces, and the like. In various embodiments, interface 911 may also be a wired connection or a bus with appropriate communications ports.

In addition, various very high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate media. In some cases, they may also include an independent processor and, in some instances, volatile RAM. The independent processors may control such communications intensive tasks as packet switching, media control and management.

According to particular example embodiments, the processing device 900 uses memory 903 to store data and program instructions and maintain a local side cache. The program instructions may control the operation of an operating system and/or one or more applications, for example. The memory or memories may also be configured to store received metadata and batch requested metadata.

Because such information and program instructions may be employed to implement the systems/methods described herein, the present invention relates to tangible, machine readable media that include program instructions, state information, etc. for performing various operations described herein. Examples of machine-readable media include memory devices such as non-volatile memory devices, volatile memory devices, and may also utilize optical media such as CD-ROM disks and DVDs, and hardware devices that are specially configured to store and perform program instructions, such as read-only memory devices (ROM) and programmable read-only memory devices (PROMs). Examples of program instructions include both machine code, such as produced by a compiler, and files containing higher level code that may be executed by the computer using an interpreter.

While the present disclosure has been particularly shown and described with reference to specific embodiments thereof, it will be understood by those skilled in the art that changes in the form and details of the disclosed embodiments may be made without departing from the spirit or scope of the disclosure. Specifically, there are many alternative ways of implementing the processes, systems, and apparatuses described. It is therefore intended that the invention be interpreted to include all variations and equivalents that fall within the true spirit and scope of the present invention. Moreover, although particular features have been described as part of each example, any combination of these features or additions of other features are intended to be included within the scope of this disclosure. Accordingly, the embodiments described herein are to be considered as illustrative and not restrictive.

What is claimed is:

1. A method comprising:
generating, using one or more processors, at least one sleep model based, at least in part, on reference data, the at least one sleep model being configured to identify an estimated sleep age of at least one user based on an input;
receiving measurement data comprising data values representing measurements of neural activity of the at least one user;
generating, using the one or more processors, the estimated sleep age of the at least one user based, at least in part, on the at least one sleep model and the received measurement data;
generating, using the one or more processors, a plurality of stimulation parameters based, at least in part, on the estimated sleep age, the plurality of stimulation parameters being configured to modify the estimated sleep age of the at least one user; and
applying a stimulus to a brain of the at least one user based on the generated plurality of stimulation parameters.

2. The method of claim 1, wherein the reference data is aggregated from a plurality of users.

3. The method of claim 1, wherein the at least one sleep model comprises a data structure configured to map the received measurement data to one of a plurality of estimated sleep ages.

4. The method of claim 1, wherein the estimated sleep age is generated based on a plurality of performance metrics.

5. The method of claim 4, wherein the plurality of performance metrics comprises sleep onset latency, variability of biometrics, and relative percentages of sleep stages.

6. The method of claim 1, wherein the modifying of the estimated sleep age comprises:
changing a sleep age of the at least one user to a target sleep age.

7. The method of claim 6, wherein the plurality of stimulation parameters comprise multi-modal stimulation.

8. The method of claim 7, wherein the multi-modal stimulation comprises at least two of electrical stimuli, tactile stimuli, visual stimuli, and auditory stimuli.

9. The method of claim 1 further comprising:
generating an estimated wake age based on a wake model.

10. A system comprising:
a communications interface configured to receive measurement data comprising data values representing measurements of neural activity of at least one user;
a processing device configured to:
generate at least one sleep model based, at least in part, on reference data, the at least one sleep model being configured to identify an estimated sleep age of the at least one user based on an input;
generate the estimated sleep age of the at least one user based, at least in part, on the at least one sleep model and the received measurement data; and
generate a plurality of stimulation parameters based, at least in part, on the estimated sleep age, the plurality of stimulation parameters being configured to modify the estimated sleep age of the at least one user; and
a memory device configured to store the at least one sleep model and the plurality of stimulation parameters;
wherein the communications interface is further configured to apply a stimulus to a brain of the at least one user based on the generated plurality of stimulation parameters.

11. The system of claim 10, wherein the at least one sleep model comprises a data structure configured to map the received measurement data to one of a plurality of estimated sleep ages.

12. The system of claim 10, wherein the estimated sleep age is generated based on a plurality of performance metrics.

13. The system of claim 10, wherein the modifying of the estimated sleep age comprises:
changing a sleep age of the at least one user to a target sleep age.

14. The system of claim 10, wherein the plurality of stimulation parameters comprise multi-modal stimulation.

15. The system of claim 10 wherein the processing device is further configured to:
generate an estimated wake age based on a wake model.

16. A device comprising:
a communications interface configured to receive measurement data comprising data values representing measurements of neural activity of at least one user; and
one or more processors configured to:
generate at least one sleep model based, at least in part, on reference data, the at least one sleep model being configured to identify an estimated sleep age of the at least one user based on an input;
generate the estimated sleep age of the at least one user based, at least in part, on the at least one sleep model and the received measurement data; and
generate a plurality of stimulation parameters based, at least in part, on the estimated sleep age, the plurality of stimulation parameters being configured to modify the estimated sleep age of the at least one user;
wherein the communications interface is further configured to apply a stimulus to a brain of the at least one user based on the generated plurality of stimulation parameters.

17. The device of claim 16, wherein the at least one sleep model comprises a data structure configured to map the received measurement data to one of a plurality of estimated sleep ages.

18. The device of claim 16, wherein the estimated sleep age is generated based on a plurality of performance metrics.

19. The device of claim 16, wherein the modifying of the estimated sleep age comprises:
changing a sleep age of the at least one user to a target sleep age.

20. The device of claim 16, wherein the plurality of stimulation parameters comprise multi-modal stimulation.

* * * * *